(12) United States Patent
Ryu et al.

(10) Patent No.: US 11,877,732 B1
(45) Date of Patent: *Jan. 23, 2024

(54) SHAPE SENSING BIOPSY NEEDLE

(71) Applicant: Intelligent Fiber Optic Systems Corporation, San Jose, CA (US)

(72) Inventors: Seok Chang Ryu, Stanford, CA (US); Mark Cutkosky, Palo Alto, CA (US); Richard J. Black, Menlo Park, CA (US); Joannes Mario Costa, Rancho La Costa, CA (US); Behzad Moslehi, Los Altos, CA (US); Fereydoun Faridian, Atherton, CA (US); Levy Oblea, Union City, CA (US); Vahid Sotoudeh, Los Altos, CA (US)

(73) Assignee: Intelligent Fiber Optic Systems Corporation, Milpitas, CA (US)

( * ) Notice: Subject to any disclaimer, the term of this patent is extended or adjusted under 35 U.S.C. 154(b) by 920 days.

This patent is subject to a terminal disclaimer.

(21) Appl. No.: 16/866,274

(22) Filed: May 4, 2020

Related U.S. Application Data

(63) Continuation of application No. 14/034,767, filed on Sep. 24, 2013, now Pat. No. 10,675,008.

(51) Int. Cl.
*A61B 10/02* (2006.01)
*A61B 10/04* (2006.01)
(Continued)

(52) U.S. Cl.
CPC .......... *A61B 10/0275* (2013.01); *A61B 10/04* (2013.01); *A61B 17/3421* (2013.01); *A61B 2010/045* (2013.01); *A61B 2017/003* (2013.01)

(58) Field of Classification Search
CPC . A61B 10/0275; A61B 10/04; A61B 17/3421; A61B 2010/045;
(Continued)

(56) References Cited

U.S. PATENT DOCUMENTS 5,152,748 A * 10/1992 Chastagner ............ A61B 10/06
604/95.05
5,231,989 A * 8/1993 Middleman ....... A61M 25/0147
604/95.01

(Continued)

*Primary Examiner* — Rene T Towa
(74) *Attorney, Agent, or Firm* — File-EE-Patents.com; Jay A. Chesavage

(57) ABSTRACT

A biopsy needle has a cylindrical shell outer cannula and a stylet consisting of an inner stylet and outer stylet, both of which are inserted into the cylindrical cannula. The outer stylet has a series of strain relieved slits which provide bending over a deflection region in one direction, and the outer stylet is formed from a material such as a shape memory alloy (SMA) having a superelastic phase. The deflection is generated by an SMA wire spanning a deflection extent and attached to the outer stylet on either side of the deflection extent. The inner stylet, when positioned inside the outer stylet, has one or more actuation fibers which couple optical energy into the SMA wire, causing a deflection of the outer stylet over the deflection extent, with the optical energy provided to the actuation fibers for control of the deflection. Additional fibers may be placed in the inner stylet to measure temperature and to measure deflection.

21 Claims, 6 Drawing Sheets

(51) Int. Cl.
*A61B 17/34* (2006.01)
*A61B 17/00* (2006.01)

(58) Field of Classification Search
CPC .......... A61B 2017/003; A61B 10/0233; A61B 34/20; A61B 2017/00084; A61B 2017/00309; A61B 2017/00853; A61B 2017/00867; A61B 2017/00907; A61B 2017/12072; A61B 2034/2061
See application file for complete search history.

(56) References Cited

U.S. PATENT DOCUMENTS

| | | | | |
|---|---|---|---|---|
| 8,649,847 | B1* | 2/2014 | Park ................. | A61M 25/0105 604/95.05 |
| 2005/0149062 | A1* | 7/2005 | Carroll ............... | A61B 17/3478 606/129 |
| 2009/0192495 | A1* | 7/2009 | Ostrovsky ......... | A61M 25/0138 604/528 |

\* cited by examiner

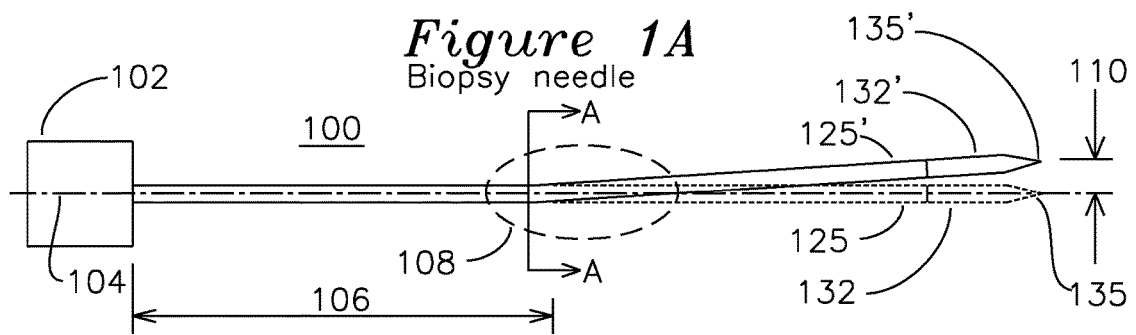
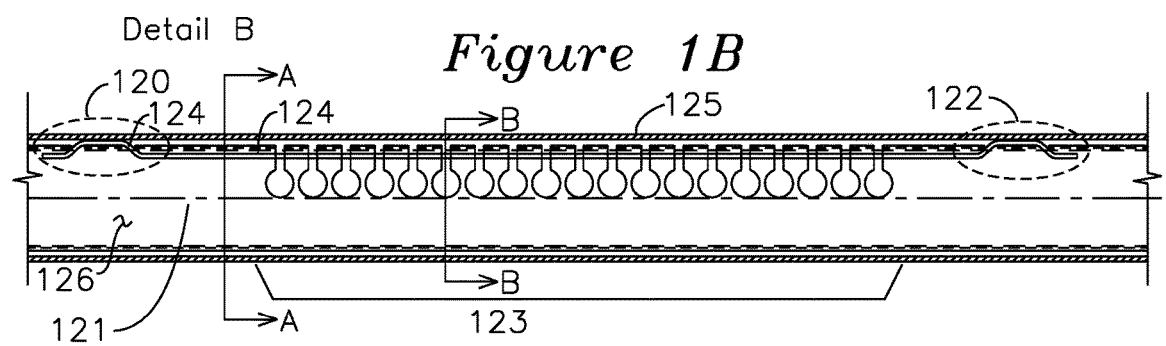
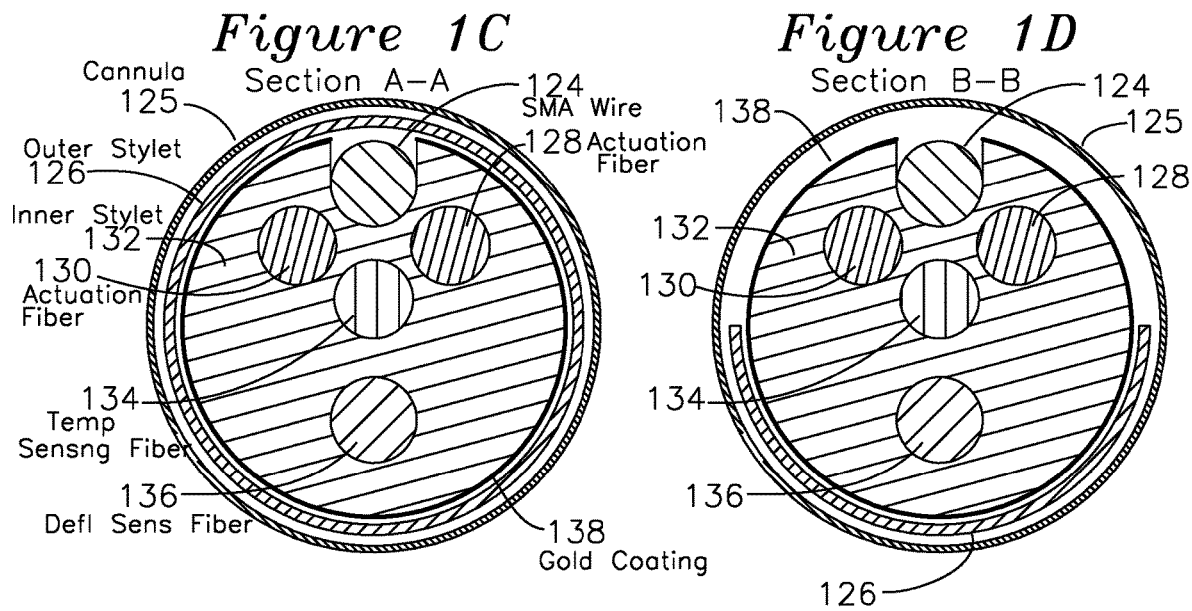

Detail B

Side View – undeflected

Top View – undeflected

Side View – deflected

Optical Biopsy Needle Deflection and Shape Sensing System

Vertical Deflection vs Time

Experimental (o) vs Simulated FEA (□) stiffness

Wire displacement — Optical vs Joule heating

Steerable Biopsy Needle with Slitted Shape Sensing Fiber

SHAPE SENSING BIOPSY NEEDLE

The present invention was developed under SBIR award No. 1142378 granted by the National Science Foundation (NSF) and NIH grant SBIR R43-EB011822. The government has certain rights in this invention.

FIELD OF THE INVENTION

The present invention claims priority to U.S. patent application Ser. No. 14/037,767 filed Sep. 24, 2013.

The present invention relates to a biopsy needle. In particular, the invention relates to a biopsy needle which is steerable and provides for measurement of deflection angle using shape sensing.

BACKGROUND OF THE INVENTION

In the field of interventional radiology, procedures such as biopsies or punctures are performed in combination with an imaging device which provides guidance during the biopsy procedure to a region of interest for the tissue sample. Magnetic Resonance (MR) scanners are useful imaging devices in this context: the radiologist and the patient are not exposed to any ionizing radiation, and the images provided by MR scanners provide a high level of contrast and sufficient resolution to identify small structures such as early stage tumors.

One of the factors limiting the accuracy of such guided biopsy techniques is needle deflection during the needle insertion. The control of the needle path, previously achieved with a rigid needle body assumption, thus evolved towards needle steering by including needle-tissue interaction models, to predict the behavior of the needle from its geometry and tissue modeling. In one prior art system, the needle is simply rotated by 180° when the estimated deflection reaches a given threshold. More complex control strategies have subsequently been developed to compensate for needle deflections and even to avoid anatomical obstacles. In another prior art system, the needle is manipulated from its base, outside the patient body, using a robotic system to create forces and moments on the needle in a similar way to the approach used by clinicians. The stiffness of the tissues at the entry point may limit such a steering strategy, and a robotic system relying on this technique would require mobility in addition to those required for needle insertion and rotation about the needle long axis.

In another prior art device, relative displacements between concentric needles, or a pre-bent needle integrated into a straight cannula, are used to generate a needle trajectory.

The design of an active needle has long been considered of interest, but a primary difficulty for guided use is MR compatibility, due to the interaction between the needle and the magnetic field and RF fields generated by the MR scanner. For example, one prior art system uses a needle with a magnetized compliant section near the tip that is controlled by an external magnetic force, which is not MR-compatible. The thin tip also makes the needle susceptible to buckling. Another prior system utilizes a piezoelectric material deposited on the needle to create a continuous bending effect along the needle. However, this design is not optimized for steering the needle tip during insertion. Another prior art system uses a tendon-driven steerable needle, and has been used for lung biopsy procedures, where tissues are much less dense than in the prostate.

The principle of an active needle can also be related to active catheters for navigation in blood vessels, however this type of design cannot be directly exploited for an active needle because of the very different mechanical interactions that exist between a needle and tissues, as compared to the controlled movement of a catheter which is guided by vessel walls.

MR-compatible actuation technologies have also been developed for robotic devices. Pneumatic or hydraulic actuation systems are of interest, the latter presenting an impressive power/volume ratio. However, integrating such technologies in a 1-2 mm diameter needle has not been possible and specific new risks to the patient are presented by the introduction of these methods in a needle biopsy requiring a higher level of active guidance and steering.

It is desired to provide an MR compatible needle which is steerable through a combination of needle deflection and rotation about the needle long axis during and throughout the needle insertion process and provide guidance to a biopsy site.

OBJECTS OF THE INVENTION

A first object of the invention is a guided biopsy needle having an outer sleeve cannula surrounding a removable steerable stylet comprising an outer stylet part and an inner stylet part, the outer stylet part having a plurality of strain relieved slots which provide bending in at least one plane, the strain relieved slots being placed over an axial extent, the outer stylet part further having a shape material alloy (SMA) which is anchored on opposite ends of the extent of strain relieved slots such that when the SMA is thermally activated, the needle deflects in a direction which reduces the gaps of the strain relieved slots, the inner stylet having longitudinal excitation fibers for coupling photonic energy to the SMA, the inner stylet also having a temperature sensor and a deflection sensor.

A second object of the invention is a guided biopsy needle having an outer stylet and an inner stylet, the outer stylet having:
  a base portion attached to the outer stylet and having a cylindrical hollow extent, a first SMA anchor extent, a deflection extent, a second SMA anchor extent, an SMA material attached in the first SMA anchor extent and also the second SMA anchor extent, the SMA material thereby spanning the deflection extent;
  the inner stylet having:
    a slot for providing clearance to the SMA material;
    at least one optical fiber coupling optical energy to the SMA in the stylet slot;
    at least one optical fiber for measuring a temperature; and
    at least one optical fiber for measuring a deflection.

SUMMARY OF THE INVENTION

A biopsy needle has an outer cannula and a removable stylet, the stylet comprising an inner stylet part and an outer stylet part, both of which are inserted into the cannula for steering and shape sensing, such as during a biopsy procedure. After steering the needle to the desired location, the stylet assembly is removed and a biopsy needle is inserted into the cannula for tissue sampling. The outer stylet is formed from a cylindrical shell or tube and has, in sequence, a base attachment extent, a first extent, a first SMA attachment extent, a deflection extent, a second SMA attachment extent, a second needle extent, and optionally, a tip. An SMA material is secured to the first SMA attachment extent and second SMA attachment extent, thereby spanning the deflection extent. The inner stylet fits inside the outer stylet and has a slot to accommodate the SMA material, and also has adjacent actuation optical fibers with a cladding and/or core modified to couple photonic energy into the SMA, causing a rise in temperature in the SMA, and for the SMA to change shape, thereby deflecting the needle. The distal end of the inner stylet may terminate in a needle tip, such that the needle tip may be formed from the outer stylet with the inner stylet placed inside the outer stylet, or the needle tip may be formed from the inner stylet, and thereafter placed into the outer stylet to form the removable stylet assembly. The cladding and/or core modification of the actuation optical fibers may include etching or side polishing of the cladding of multi-mode fibers to allow regions of optical emission coupling to the SMA, or tilted fiber gratings written into single mode fibers which couple optical energy to the SMA, or a combination of the above. The outer stylet may also be formed from an SMA with a superelastic mode to increase deflection during the photonic activation state. The inner stylet additionally provides structures for preferential coupling of activation optical energy into the SMA material, and in one embodiment, includes a reflective coating on the outer cylindrical surfaces of the stylet which increase the coupling of activation energy from the actuation optical fiber to the SMA material. The inner stylet also provides for a temperature measurement sensor and a deflection sensing fiber.

In one embodiment of the invention, the actuation fiber is a single-mode fiber with internal angled gratings formed in the core of the fiber which couple optical energy out of the fiber and to the SMA, and the temperature sensing fiber may comprise a fiber Bragg grating (FBG) which is coupled to a single port wavelength interrogator for measurement of the deflection, with the temperature measurement used to limit the actuation energy level and also compensate for measurements made with the deflection sensing fiber.

BRIEF DESCRIPTION OF THE DRAWINGS

FIG. 1A is a side view of a biopsy needle.

FIG. 1B is a detail side view of a steering region of the needle.

FIG. 1C is a section view of FIG. 1B.

FIG. 1D is a section view of FIG. 1B.

DETAILED DESCRIPTION OF THE INVENTION

Figure 1E:
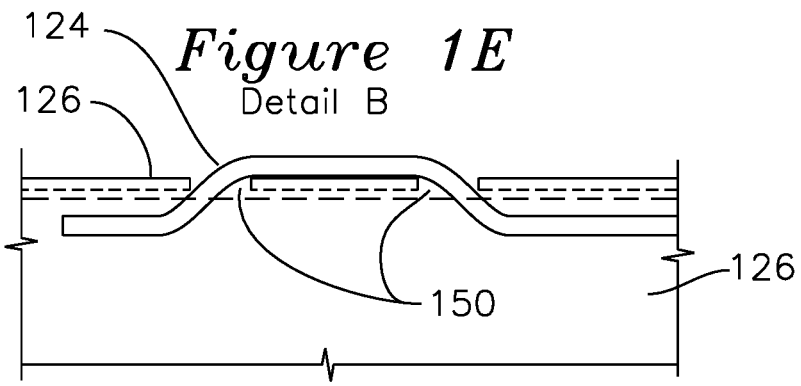
FIG. 1E is a section view of FIG. 1B.

FIG. 1A shows the active elements of a steerable biopsy needle 100, including a cannula 125 which is optionally covered with a Teflon sheath or tube (not shown) to provide thermal isolation between the surrounding tissues and the thermally activated elements of the needle. According to a general object of the invention, the needle is steered using the axial asymmetry of the needle to create forces on the needle during its insertion. In this embodiment, the primary degrees of freedom to control needle direction are the insertion geometry and the axial rotation of the needle. Needles with asymmetric bevels at the tip are submitted to an unbalanced field of forces during the insertion. This phenomenon can be used to steer thin needles. Various complex insertion trajectory curves may be obtained by combining the needle insertion and self-rotation movements about the long axis 104 of the needle. The region of deflection 108 may be placed a distance 106 from the needle base 102, which is rotated during placement and deflection to guide the biopsy needle to the desired location.

The biopsy needle of FIG. 1A is capable of active bending that, in combination with the normal insertion forces and the ability to rotate the needle about its long axis 104, allows it to be steered to reach small tumors or other sites. The actuation system which will be described is entirely compatible with MR imaging and the overall needle diameter in one embodiment is 1.65 mm, which is compatible with standard prostate biopsy needles.

Among the actuation technologies that present a high power/volume ratio and MR-compatibility, Shape Memory Alloys (SMA) are of particular interest, and when formed as a wire, provide a high specific force combining a large mechanical strain with a large force to volume ratio. By activating thermally a phase transition in the SMA microstructure, this material can be used as an actuator, and in one embodiment, the thermal activation is accomplished using optical energy.

Joule heating with an electric current is one method of activation to obtain SMA contraction. An MR-compatible device can be designed using such an approach. However, imaging artifacts will be created from the co-generated SMA current magnetic fields if actuation and MR imaging are performed concurrently.

The present biopsy needle of the present invention provides an outer cannula 125, into which is inserted a stylet composed of two main parts as shown in the views of FIGS. 1A, 1B, 1C, and 1D: an inner stylet 132 and an outer stylet 126. During a biopsy, the two stylet elements 132 and 126 are inserted together into the cannula 125 to form the biopsy needle, and the stylet is activated to steer and sense the shape of the needle as the needle assembly is guided to reach the biopsy site. Then, the stylet comprising the outer stylet 126 and inner stylet 132 are removed together, and a biopsy probe is inserted through the cannula 125 to perform the biopsy. In one embodiment of the invention shown in FIGS. 1A, 1B, 1C, and 1D, the active element is an SMA wire 124 attached to the outer stylet 126 on opposite sides of a deflection extent 123, and is activated by optical energy conveyed by fibers in the inner stylet 132 which couple to the outer stylet 126 and steer the cannula 125. The inner stylet 132 and outer stylet 126 are separate coaxial structures such that the outer stylet 126 deflection is not impeded by the inner stylet 132 during deflection, and it is preferable for friction between the outer surface of the inner stylet and the inner surface of the outer stylet be minimized, and the photonic coupling from actuation fibers 128 and 130 to the SMA wire 124 to be minimized. In a preferred embodiment, the tip extent of the needle includes tip 135 which is formed from a metal such as stainless steel or any biocompatible material and fastened to a distal end of the multi-lumen inner stylet 132, and the needle tip 135 tapers to a point on the main axis 104, although it is possible for the tip 135 to form a point adjacent to the outer radius of the stylet, such as a prior art planar beveled cut at the needle tip.

The active element SMA wire 124 introduces one degree of freedom in the needle body. Combining active bending with needle insertion and axial 104 rotation movements, it becomes possible to control the needle trajectory, following a similar approach as used previously for needle steering with beveled tip needles.

In a preferred embodiment, the inner stylet 132 has a maximum diameter of substantially 1.35 mm, at the location of the active element 124, corresponding to an 18G biopsy needle. With the outer stylet 126 and external cannula 125, the overall diameter is equal to 1.65 mm, which is equivalent to 16 G devices used for prostate biopsies.

FIG. 1C shows a cross section view A-A of FIG. 1B and FIG. 1D shows a cross section view B-B through one of the slotted strain relieved cuts in the deflection extent 123. The SMA for actuation 124 is formed as a wire with attachment points at SMA attachments 124 and 122, and continues through the deflection extent. The SMA wire 124 is activated with side optical heating through photonic energy coupled into actuation fibers 128 and 130. To promote compactness and effective heat transfer, the actuation optical fibers 128 and 130 run parallel to the needle axis 104 and transmit heat over a finite length of the SMA wire 124 such as the deflection extent 123 and oriented in the axial 104 direction to get a sufficient needle displacement (shown as FIG. 1A deflected components 132' and 125' compared with undeflected components 132 and 125). Additionally, to improve photonic coupling from the actuation fibers 128,130 to the SMA 124, the outer surface of the stylet 132 may be coated with a reflective material 138 such as gold which reflects infrared (IR) optical energy, the coating excluding the slot in the stylet supporting the SMA wire 124, to ensure that optical energy from the actuation fibers 128 and 130 is optimally coupled into the SMA wire 124 and is not lost to leakage outside the stylet 132. Several different forms of actuation fibers 128 and 130 are possible for coupling optical energy from the actuation fibers 128 and 130 to the SMA 124.

In one embodiment of the invention, the actuation fibers 128 and 130 are multi-mode fibers and have a cladding which is reduced in thickness on one or more regions along the axis with the regions oriented towards the SMA wire 124 to allow optical energy guided in the core to couple into the SMA wire 124. In an example embodiment, the cladding has a diameter of 125 µm, which is removed in specific regions of the fiber using a glass etching cream such as Armour Etch of Armour Products. In another example, the etching of a particular region is performed in successive etching and rinsing events, with each successive session removing substantially 6 µm of cladding. In another example, the etch process produces a region extent greater than 2 mm for coupling optical energy out of the core of the actuation fiber. In another example of the invention, the cladding is removed and a plurality of discrete regions of the actuation fiber 124 are etched, such as in etching time intervals of substantially 30 minutes, each interval removing substantially 6 µm of cladding from a fiber having a cladding diameter of approximately 125 µm and a fiber core diameter of approximately 105 µm. In a preferred embodiment of the invention, each etching region has a depth of etching which provides levels of optical energy to exist at each region, thereby providing a substantially uniform optical excitation over the extent of the SMA wire 124. In another embodiment of the invention, each successive etched region has a different etch extent, such that each successive etch region is greater than a previous region, thereby providing a uniform level of optical energy by compensating for the reduced optical energy which leaves each etch region to the subsequent etch region. Although the dimensions given correspond to those of a multi-mode fiber, it is possible to consider a single mode fiber for actuation using reduced thickness cladding as described.

In another example of the invention, the actuation fibers are multi-mode fibers which are side polished to increase the optical coupling from the core to the actuation wire 124, with the same objectives of uniform levels of power being applied to the SMA wire 124 along the active extent 124 of the SMA wire 124, or any preferable extent of the SMA wire which provides the required contraction in the SMA wire 124.

In another example of the invention, the optical energy is coupled out of the actuation fibers 128 and 130 and into the SMA wire 124 through the use of tilted fiber Bragg gratings (TFBG) written into single mode fiber (SMF). For TFBGs, by removing the fiber cladding and writing an angled grating into the core of the fiber, the power emission of optical energy entering the SMA wire 124 from the actuation fiber 128 or 130 is maximized, and can reach 55% of the laser power emitted through the fiber. In this manner, homogeneous photonic emissions leading to SMA heating can be obtained over lengths up to 50 mm of fiber. Whether side polishing or TFBGs are used, the addition of thermal cement can enhance the uniformity of thermal transfer along the SMA wire. It is also desirable to ensure that maximum coupling of optical energy out if the actuation fiber and to the SMA wire 124 is achieved, and that a minimum of input optical energy is coupled back to the source, as the optical source is typically a laser with an isolation requirement providing a minimum of reflected optical energy enter the laser output port, which tends to cause modal changes and other irregularities in temporal uniformity. A linearly polarized laser optical source may reduce this isolation requirement.

To enhance uniform thermal coupling of optical energy to the SMA fiber 124 where specific regions of emission are used, the specific regions of optical side emission along the axis of the actuation fibers may be staggered. For example, if each actuation fiber has four discrete regions of optical emission, and the four regions are directed in the same azimuthal angle of the fiber axis, and the axial separation is D between emitting regions, the two fibers may be axially offset from each other by a distance of D/2, thereby providing optical energy every D/2 axial distance over the actuation extent of the SMA wire 124.

In one embodiment of the invention, the use of SMA materials for MR compatible guidance is also used to provide superelastic structures in outer stylet 126. The phase transition of SMA 124 may be used for actuation, but also in the outer stylet 126 to provide the flexibility needed to deflect the needle. SMA exhibits a so-called superelastic domain known as the austenite phase when the SMA temperature is sufficiently high. A stress increase can then induce a phase transition towards the martensite phase. This stress-induced phase transition is characterized by a large plateau in the stress-strain domain, providing increased deflection for a given applied force. In one embodiment of the present invention, this large elasticity domain is optionally used for the outer stylet 126 or stylet 132 of the active device. This approach allows the needle to achieve high deflections, due to device actuation or to interaction with tissues, and without plastic deformation.

Figure 1F:
FIG. 1F is a side view of an undeflected biopsy needle.
Figure 1G:
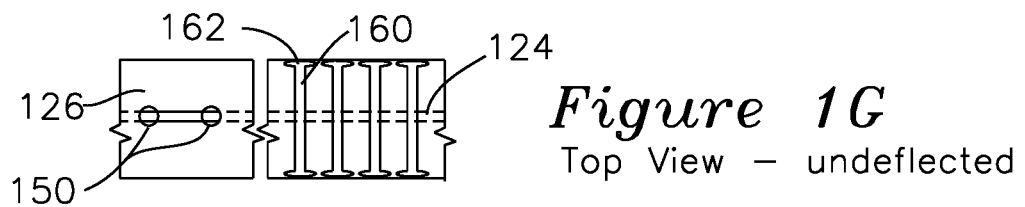
FIG. 1G is a top view of an undeflected biopsy needle.
Figure 1H:
FIG. 1H is a side view of a deflected biopsy needle.

In one embodiment of the invention as shown in FIGS. 1B, 1C, 1D, 1E, 1F, and 1G, the actuation mechanism is based on a laser machined SMA tube which forms the outer stylet 126 and SMA wire 124 which forms the active element attached to the outer stylet in first attachment extent 124 and second attachment extent 122. The flexible deflection extent 123 of the outer stylet 126 is formed from SMA tube and is 25 mm long, with a series of slits 160 with rounded ends 162 (to reduce stress concentrations) on one side or on both sides, as shown in FIGS. 1F and 1G. The rounded end 162 for reduction of stress concentration may take the form of a circular cut 162 joined with slit 160, with the bottom edge of the circle tangent to the neutral plane, shown as coincident with axis 121 of FIG. 1B. The number of slits 160 and the slit gap of 30 μm between two consecutive slits are chosen so that the 30 μm gap of each slit closes fully under maximum actuation. In this way, the device is always in a configuration for which the wire can generate a tension during its contraction, independent of the external interaction forces. Once the slits have closed (in the fully deflected position), the needle assembly becomes considerably stiffer with respect to additional bending loads. FIGS. 1E and 1G shows the anchor extent at one end of the outer stylet 126 which is created in one example shown by two holes 150 with the SMA wire 124 secured by threading the wire 124 through each hole 150. In an alternate embodiment, the SMA wire 124 anchoring is accomplished using a weld or other bond which minimizes stress concentrations at the anchor points of SMA wire 124 which could reduce the SMA wire life.

In addition to the SMA wire 124, which in a preferred embodiment is substantially 0.254 mm, the outer stylet 126 is formed from an SMA tube which is in close proximity to various optical fibers for SMA actuation through heating and sensing through stress induced in the SMA wire 124 from the actuation fibers 128,130. These elements, presented in the following section, are inserted in a flexible multi-lumen polytetrafluoroethylene (PTFE) tube which forms the body of stylet 132 to obtain and maintain their alignments. High density PTFE material is relatively transparent to infrared (IR) light, which in the present patent is understood to be in the range from 800 nm to 2500 nm wavelength, although optical fiber operates at preferably lowest attenuation in approximate wavelength ranges of 1550 nm±50 nm. Typical single mode optical fiber has greater attenuation at shorter wavelengths, however economical optical sources operate in the 850 nm and 1300 nm wavelength ranges compared to 1550 nm sources. This IR transparency allows most of the emitted power from the actuation fibers 128 and 130 to reach the SMA wire 124. A sputtered 500 nm gold coating 138 on the outer surfaces of the stylet 132, excluding the slot which supports SMA wire 124, enhances coupling of IR which is internally reflected in the stylet 132 to the SMA wire 124. In one embodiment of the invention, the stylet 132 is extruded high density PTFE resin with the extrusion die forming the slot for SMA wire 124, and channels for actuation fibers 128 and 130, temperature sensing fiber 134, and deflection sensing fiber 136. In another embodiment of the invention, the stylet is fabricated from surgical grade silicon. The tip 132 is typically fabricated from a metal such as stainless steel and bonded to the distal end of the stylet.

In one embodiment of the invention, the SMA wire has a diameter of substantially 0.25 mm. In a preferred embodiment, Flexinol wire is used, which can generate, according to the manufacturer's specifications, up to 4% of strain when heated to 90° C., and the optical energy delivered to the actuation fibers 128, 132 is provided by in infrared source such as a 976 nm laser providing greater than 0.5 W of power to each optical fiber for distributed delivery to the SMA wire 124. The 90° C. temperature is high compared to safe temperatures for human tissues, which are on the order of 45° C. However, in a preferred embodiment, at least one of the active element SMA wire 124 or superelastic deformation region 124 of the outer stylet 126 formed from SMA is heat treated to lower the phase transition temperature to 55° C. In a preferred embodiment of the invention, the outer stylet 126 is coated or placed inside a tube formed from PTFE, which introduces an additional thermal insulation with respect to tissue. Moreover, the bending actuation will be applied only for short periods of time, to alter the path taken by the needle as it is inserted. Under these conditions, surrounding tissues would be able to sustain the resulting temperature increases. Two actuation fibers, 128 and 130, are embedded in the device to heat the SMA wire 124. Each actuation fiber integrates a side heating element so that four heating areas, including the fiber tips, are positioned along the 18 mm extent 123 of SMA wire.

In a preferred embodiment, MR-compatible optical sensing of position is provided. In addition to the actuation fibers 128 and 130, a temperature sensing optical fiber 134 with standard FBGs provides temperature sensing. In one embodiment of the invention, a deflection strain sensing fiber 136 has a treated section which increases light loss as a function of curvature. Such a shape sensing fiber can be constructed by coating the distal tip (closest to the needle tip 135) of the fiber with sputtered gold, machining a series of slits into the cladding and which are perpendicular to the axis of the fiber, such that bending the fiber reduces or increases the optical loss for reflected optical energy, illuminating the opposite end of the fiber through a coupler or circulator, and measuring the reflected optical energy to the other port of the circulator. In one example embodiment of the invention, the shape sensing fiber is unjacketed plastic fiber with 250 μm cladding diameter, and 240 μm core diameter, with eight slits having a spacing of 300 μm, starting 10 mm from the needle tip, centered on the active element SMA wire 124, with the tip polished with fpm abrasive and sputter coated with a 500 μm deposition layer of gold. On advantage of the shape sensing fiber fabricated in this manner is that is may be placed into the lumen of the stylus freely, as it does not need to be anchored in the lumen as is the case with FBG gratings measuring strain, with the fiber bonded to the lumen at one end to prevent rotation of the bending sensor in the lumen.

Figure 6:
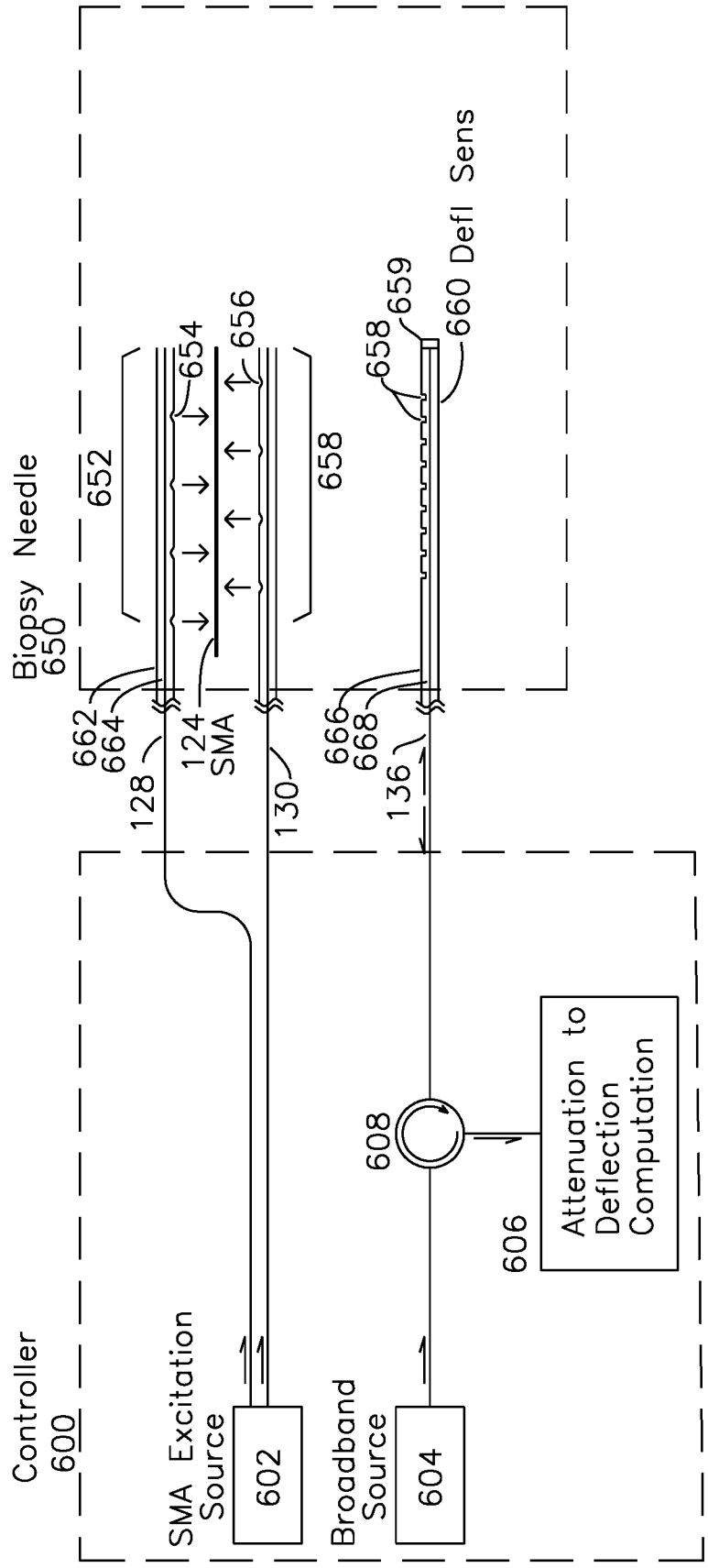
FIG. 6 is a block diagram of a steerable biopsy needle.

FIG. 6 in combination with FIG. 1C shows an example embodiment of the slitted shape sensing fiber 218, which is shown in certain views as expanded in biopsy needle 650 to include the core 668 and cladding 666, with the cladding having slits 658 and distal end coated with reflective gold 658. As the needle is deflected, the slits 658 have gaps which close or open to increase or decrease coupling through the fiber. There are several advantages of using the opening and closing of slits to perform shape sensing. One advantage is that the attenuation-based shape sensing fiber 136 may be freely positioned in the associated lumen, and is not secured in position, since the attenuation characteristics are deflection dependent, and not strain dependent, as in the case of FBGs placed in fiber 136. Using the attenuation fiber 136 shown in FIG. 6, when the needle is bent in a direction which increases the gaps, optical energy from broadband source 604 travelling through circulator 608 and coupled to fiber 218 is attenuated in the core 668 as it passes through the gaps 658, reflects from coated 659 end, counter propagates through slits 658, and is coupled through circulator 608 to amplitude sensor 606, which correlates amplitude to deflection. For SMA wire 252 activation, and as was described earlier, power in excess of 0.5 W is propagated through fibers 214 and 216, which are shown including core 664 and cladding 662, which has etched regions 654 and 656 which couple optical energy in staggered physical locations to SMA wire 252. The optical energy causes a thermal change in wire 252, which may shrink, causing deflection of the needle, which is sensed by deflection sensor 660. Temperature sensing fiber 134 is optional, and when present, operates as was previously described—hence it is not shown in this view for clarity.

In another embodiment of the invention, strain sensing fiber 136 of FIGS. 1C and 1D has an FBG embedded in a location which senses strain during elongation, thereby providing a reflected wavelength shift which can be used, in combination with a temperature measurement such as from fiber 134, to determine a deflection. The estimated curvature information can be converted into mechanical strain along the temperature sensing fiber 134 and the SMA wire 124. The strain-compensated temperature and the strain on the SMA wire 124 enable closed loop control of bending angle. This bending angle can also be used to estimate the needle shape, for instance to track the needle tip in the image plane.

One embodiment of the invention provides for dual-mode gratings, which may be formed in several different ways, as will be described. It is known that estimating strain in an FBG from the shift in reflected FBG wavelength requires an accurate temperature measurement to compensate for wavelength shift associated with temperature gradients and drifts. For the configuration of FIGS. 1C and 1D, where temperature sensor 134 and strain sensor 136 are FBGs, it may occur that a temperature gradient exists from actuating fibers 130 and 128 to strain sensing FBG 136, such that temperature sensing FBG 134 is not able to accurately sense the temperature of strain sensor 136 to provide temperature compensation information. To solve this problem, in one embodiment of the invention, "dual mode gratings", or dual mode FBGs with different wavelength responses may be written in the same sensing region of optical fiber 136, such that reflection of two different wavelengths occurs. In this mode of operation, each dual mode FBG reflects wavelengths according to the differential relationship:

$$\Delta\lambda 1 = \alpha 1 * \Delta T + \beta 1 * \Delta S$$

$$\Delta\lambda 2 = \alpha 2 * \Delta T + \beta 2 * \Delta S$$

where:
α1 and α2 are temperature coefficients for wavelengths λ1 and λ2, respectively, which are typically known a priori or are characterized;
β1 and β2 are strain coefficients for wavelengths λ1 and λ2, respectively, which are typically known a priori or are characterized;
ΔT is the temperature change for the dual mode grating; and ΔS is the change in strain for the dual mode grating.

Using the above linear relationships, it is therefore possible to make a single measurement of the two reflected optical wavelengths Δλ1 and Δλ2, and solve for ΔT and ΔS from prior knowledge of α1, α2, β1, and β2. As is known in the art of solving linear equations, the resolution of wavelength or temperature is improved when the ratio of α1/α2 and β1/β2 is maximized or minimized. In this manner, a single dual mode FBG may be used for fiber 136, which removes the need for temperature measurement fiber 134. In another embodiment of the invention, dual mode gratings can be formed from a single FBG having one reflection response at λ1, and using the second natural response at the half wavelength response λ2=λ1/2, and relying on the different α and β coefficients at these two separated wavelengths. In another dual mode grating embodiment of the invention, two separate optical fibers with maximized or minimized α1/α2 and β1/β2 coefficient ratios are spliced together and have FBGs written on them such that the two separate gratings span the same sensing region, thereby providing that the two reflected wavelengths λ1 and λ2 can be in the same wavelength region, and relying on the coefficient ratios between the two types of fibers for improved resolution.

Steering performance is intrinsically linked to the steering control strategy and the mechanical properties of the tissues in interaction with the needle 100. A first mechanical property is the maximum deflection of the needle when no force is applied on the needle tip. This deflection describes the achievable trajectory correction when using a simple retract-reinsert strategy, where the needle is almost completely retracted, deflected, and inserted again. The second mechanical property is the needle stiffness, which is estimated using a very simple interaction model based on the potential behavior of the device in tissue.

Figure 2:
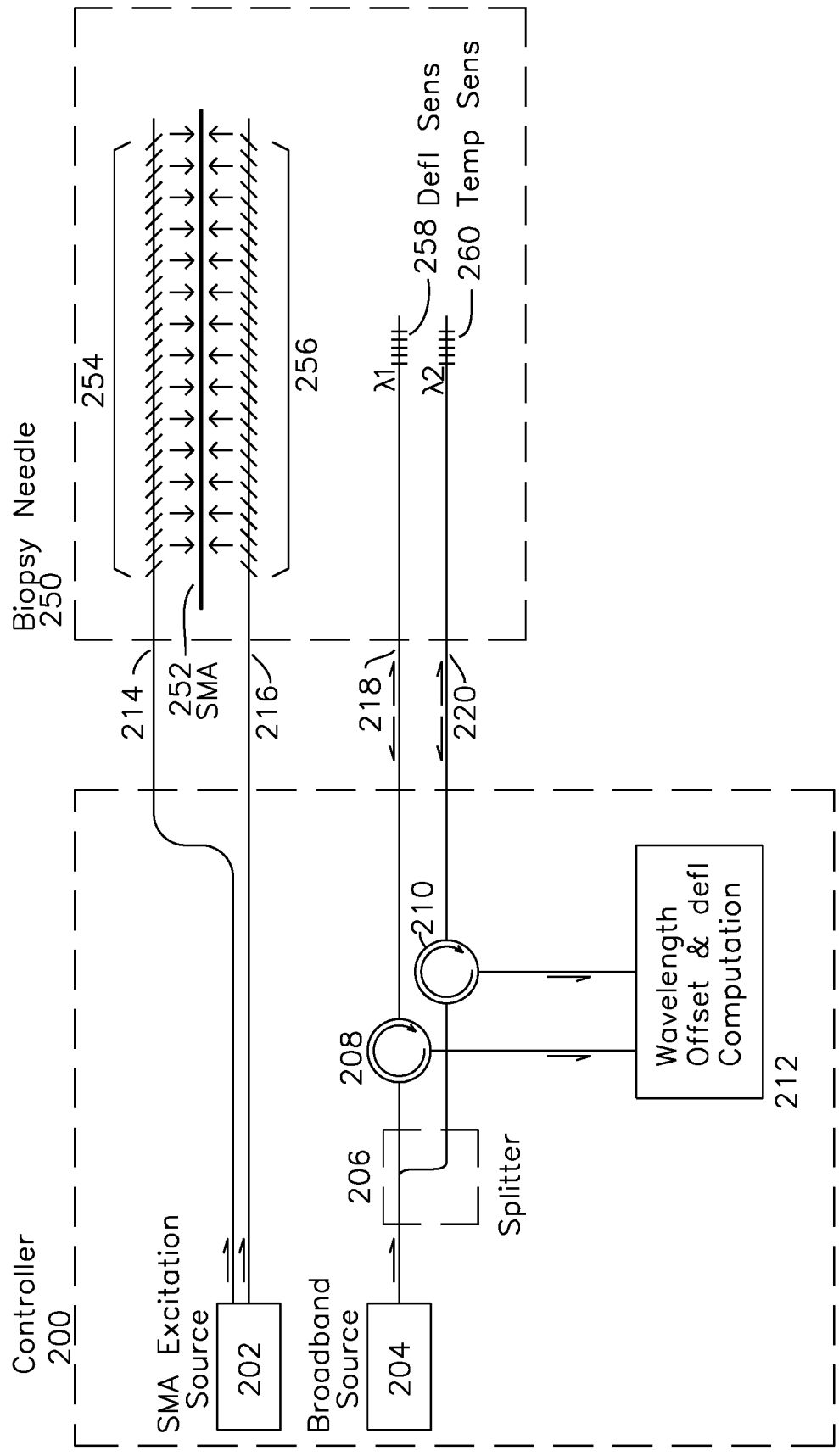
FIG. 2 is a block diagram of a controller coupled to a steerable biopsy needle.

FIG. 2 shows an example all-optical needle deflection and shape sensing controller 200 coupled to a biopsy needle 250 such as was previously described, including FIGS. 1B, 1C, 1D, and 1E. Actuation fibers 214 and 216 (corresponding to actuation fibers 128 and 130 of FIG. 1C or 1D) couple optical energy from an SMA excitation source 202 to the SMA actuator 254. In one example embodiment, the actuation fibers 214 and 216 have angled gratings written into the core over extent 254 and 256, which couple optical energy into SMA 252 (such as SMA wire 124 of FIGS. 1C and 1D), generating thermal excitation which provides the SMA wire deflection as was previously described. Deflection sensor 258 and temperature sensor 260 are coupled to fibers 218 and 220, respectively, corresponding to deflection sensing fiber 136 and temperature sensing fiber 134, respectively, of FIGS. 1C and 1D. In one form of operation, excitation source 202 is periodically pulsed or operated continuously at a unique wavelength which does not interfere with temperature measurement using grating 260 and deflection sensor 258, which receive broadband optical energy from source 204, which is coupled through splitter 206 and circulators 208 and 210 to gratings 258 and 260, respectively. Reflected optical energy is coupled through circulators 208 and 210 to wavelength discriminator 212, which converts the wavelength shift to a needle shape.

For the following analysis, Finite Element Analysis (FEA) was performed using Ansys software. Superelastic behavior of the SMA can be simulated, in isothermal conditions. A mechanical simulation was performed using the SMA wire specifications provided by the manufacturer and an experimentally identified Young's modulus for the tube under the conditions of interest.

The SMA wire can be described as a spring for which displacement depends on the force generated by the phase transition in the material and the stiffness of the surrounding elements connected to the wire. The deflection is therefore evaluated in 3 steps. First, the stiffness describing the action of the flexible tube against the actuating wire is evaluated. Next, the wire behavior during contraction is determined. Then, the needle deflection is found by simulating the bending of the SMA tube with the determined loading conditions.

The axial wire stiffness is 29 N/mm, and the (asymmetric) axial stiffness of the tube is estimated using FEA at 43 N/mm. Using the wire description introduced in the manufacturer's specifications, the action of the wire on the SMA tube can thus be modeled as a 10 N force. The simulated needle deflection 110 as shown in FIG. 1A is 2.23 mm, which represents a bending angle of 4.6°, considering from the FEA results that the rotation begins at the first slit 160 on the SMA tube closest to base 102. The Von Mises stress reaches 233 MPa in the tube. The superelastic plateau is defined for the material by a stress of 520 MPa. The superelastic effect is therefore not required during contraction of the wire but may be used to remain in the elastic regime when external loads are applied. If a simple retract-reinsert strategy is employed, the deflection angle results in a trajectory deviation of 4.8 mm when the needle is inserted by 60 mm, an average length to reach the prostate during a biopsy. The device performance seems therefore relevant for the application. As outlined earlier, its performance in terms of needle steering depends on the control strategy that will be implemented.

The SMA tube is not symmetric with respect to the needle axis. As a consequence, axial forces exerted by tissues at the tip will induce bending, similar to a needle with an asymmetric bevel. Compensating for this phenomenon is straightforward, and involves rotating the needle about its long axis. It is possible to estimate the magnitude of force that will cause the slits to close up, such as those beyond which active steering is no longer possible until the needle is rotated. The bending stiffness, defined as the ratio between the moment applied on the active part of the needle and its curvature, is estimated using FEA at 1493 $Nmm^2$. Considering a very simple model of interaction with the tissue, with a purely axial force exerted on the needle tip, this force must then be equal to 12.6 N to reach the maximum deflection estimated previously. This value seems satisfactory, as the axial force only reaches, for instance, 10 N when puncturing a prostate capsule, and is significantly lower after this puncture. Lateral forces can also induce bending, but these are compensated via a combination of actuation and needle rotation.

In one embodiment of the invention shown in FIGS. 1F and 1G, the tube slits 160 with strain relief apertures 162 are laser machined on a NiTi tube. In this version of the device, the SMA wire is pressed into the SMA tube using a grooved needle, which is manufactured using electro-discharge machining (EDM).

Figure 3:
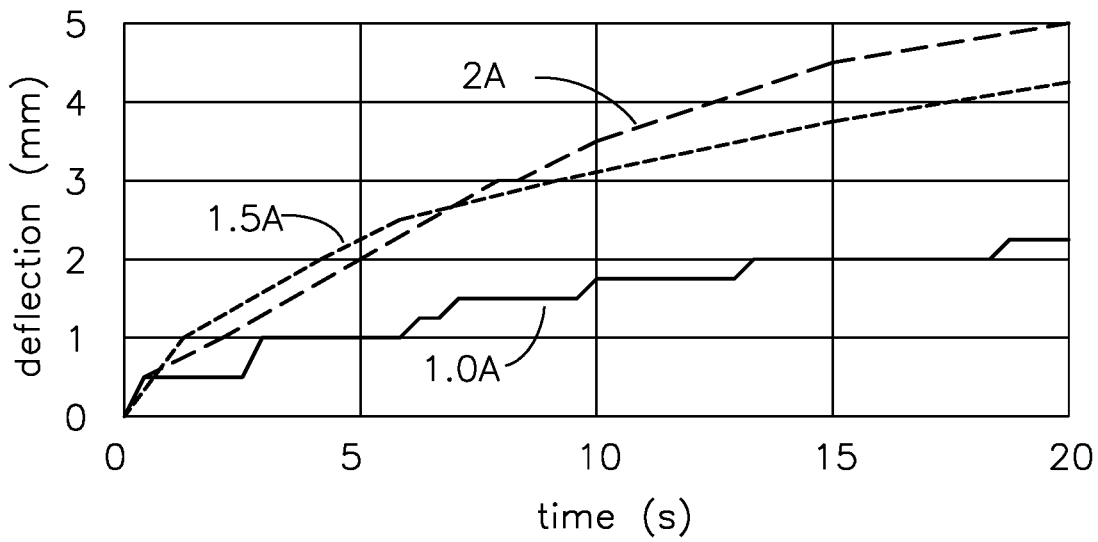
FIG. 3 is a plot of deflection versus time.

FIG. 3 shows an experimental evaluation, where the active needle SMA is activated using conventional Joule heating using current passed through the SMA wire and the outer stylet structures of FIGS. 1B, 1C, 1D, 1E 1F, and 1G. The vertical deflection 110 of FIG. 1A is evaluated using a measurement of the 15 mm long needle tip. The measurement accuracy of the tip displacement is approximately 0.17 mm, so that the angle is evaluated with an accuracy of 0.25°.

As shown in the corresponding graph of FIG. 3, heating is performed with a current of 1 A, the current suggested by the manufacturer of the SMA for this particular wire diameter. The power emitted is then 0.36 W, and the tip reaches a maximum deflection of 2.12 mm (deflection 110 of FIG. 1), within 5% of the value predicted with FEA. The current in the wire can be increased without wire breakage. Higher deflection is then observed: 4.21 mm (8.8°) and 4.98 mm (10.4°) for currents of 1.5 A and 2.0 A, respectively, as shown in FIG. 3. Stiffness evaluation is achieved by clamping the one end of the active part on a metallic breadboard to minimize the presence of any additional flexibility. Different masses are attached to a fixed point on the part to create a force perpendicular to the needle axis, and the vertical tip deflections are measured.

Figure 4:
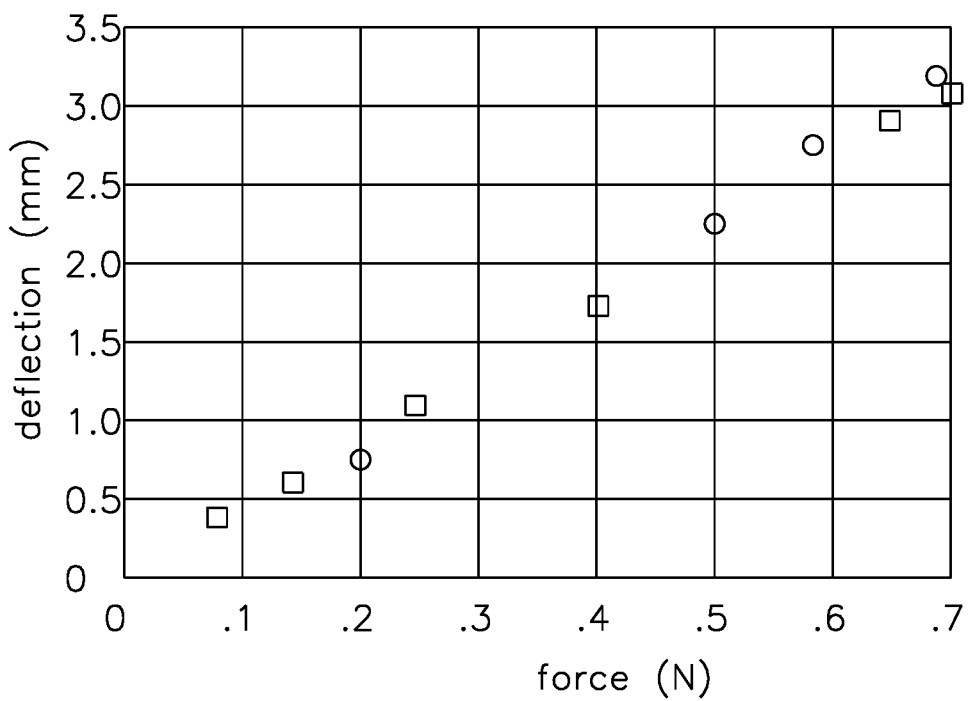
FIG. 4 is a plot of experimental measured stiffness vs. simulated stiffness.

The relationship between the displacement of the needle tip and the applied force is represented in FIG. 4 as circular symbol data points. The behavior predicted using FEA is superimposed as square symbol data points. Assuming simple beam bending, the bending stiffness of the device corresponds to 1451 $Nmm^2$, which is consistent with the expected bending stiffness. However, the prototype has a 5% lower stiffness than the value assessed numerically. The main potential source of discrepancy is the SMA behavior; the Young's modulus may be lower than expected. It is believed that the laser cutting of the slits may have affected the structure with the presence of martensite, the most flexible material phase, at room temperature.

Figure 5:
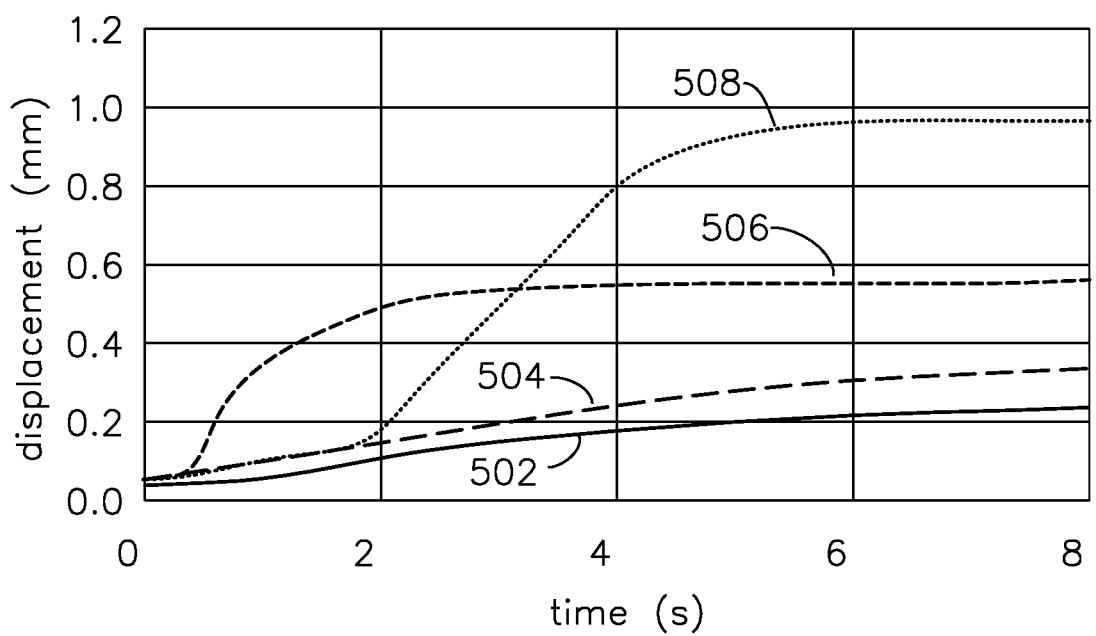
FIG. 5 is a plot of wire displacement for various forms of heating.

In one embodiment of the invention, activation optical energy is provided by two actuation multimode (105 µm core diameter) fibers with side polished or regions of the cladding etched, and coupled to 976 nm lasers. The use of two fibers allows a simulation of multi-point heating, albeit less evenly distributed than with TFBGs. The wire contraction is represented in FIG. 5. The displacements observed when using only one fiber in contact with the SMA and providing 0.38 W (curve 502), with two fibers in direct contact delivering 0.76 W (curve 504), and after displacing the two fibers 5 mm distant from the wire (curve 506), which delivers a total power of 0.32 W. The results are compared to the results obtained when the wire is heated uniformly by Joule heating using a constant current of 1.4 A (curve 508), producing 2 W for the 40 mm of wire. The dynamics and the amplitude of the contraction in this case provide a reference for the optical heating results.

The maximum power from the optical fiber tip has been evaluated. Above 0.38 W, heating with the fiber tip nearly in contact with the wire leads to the wire breakage due to the small spot size.

Using one fiber to perform the heating, the wire contraction is equal to 25% of the displacement obtained with Joule heating, with a comparable initial contraction rate. This tends to show that about 10 mm of wire has contracted during the 8 seconds of heating.

With two fibers, the total power emitted is 0.76 W. The wire displacement reaches 58% of the 40 mm wire contraction obtained by Joule heating. From a performance perspective, about 23 mm of wire is contracted with the optical heating in about 8 seconds. The initial contraction is faster than with the Joule heating. Since the heating is more localized, the wire is submitted to strong thermal gradients, and the maximum temperatures exceed those from Joule heating.

When increasing the distance between the fibers and the SMA wire, the wire no longer receives most of the power emitted by the fiber tips. Measurement with a power meter shows that each fiber sends 0.16 W to approximately 5 mm of wire. The heating effect is still significant: the wire displacement is slightly greater than obtained with a single fiber in contact, with comparable dynamics. This configuration, similar to the effect that can be obtained using side polishing or TFBGs, appears promising: the power for optical heating remains limited, with 0.32 W to obtain a contraction of more than 10 mm of wire, and heating along the length of the wire, instead of spot heating, limits overheating that can lead to breakage. With refinement of the optical heating system and of the transfer of power into the wire, the bending requirements can be satisfied.

A biopsy needle having an outer stylet and inner stylet, which is steerable with rotation of the needle in combination with controllable bending using the SMA as described may be used for many different types of procedures, including brachytherapy where the needle may be used to guide the placement of radiation seeds into a prostate, or for ablation or cryosurgical applications. Additionally, the deflection measurement may be used in combination with a control system to provide feedback in the form of power control of the laser which is coupled to the SMA wire actuation fibers.

The preceding has been a description of the preferred embodiment of the invention. It will be appreciated that deviations and modifications can be made without departing from the scope of the invention, which is defined by appended claims.

We claim:

1. A shape sensing biopsy needle comprising an outer stylet and an inner stylet surrounding a central axis,
   the outer stylet comprising a hollow cylinder, the hollow cylinder further comprising, in sequence: a base portion, a needle extent, a first Shape Memory Alloy (SMA) anchor extent, a steering extent, a second SMA anchor extent;
   the steering extent comprising a plurality of parallel slots in the outer stylet, each of the plurality of parallel slots perpendicular to the central axis and terminating in a circular aperture;
   the outer stylet also having an SMA material attached in the first SMA anchor extent and also the second SMA anchor extent and spanning the steering extent;
   the inner stylet comprising:
     a slot for providing clearance to the SMA material;
     at least one actuation optical fiber coupling optical energy to the SMA material in the inner stylet slot sufficient to cause a deflection in the steering extent of the outer stylet;
     at least one deflection measurement optical fiber for measuring a deflection, the deflection measurement optical fiber having a plurality of slots formed in the fiber cladding, the slots placed in a plane substantially perpendicular to the fiber axis, the deflection measurement optical fiber having a reflective termination.

2. The shape sensing biopsy needle of claim 1 where the slots in the fiber cladding cause a reduction in reflectivity of the optical fiber with increased deflection.

3. The shape sensing biopsy needle of claim 1 where the actuation optical fiber is a multi-mode fiber with a side polished region coupled to the SMA material in the deflection extent.

4. The shape sensing biopsy needle of claim 1 where the actuation optical fiber is a multi-mode fiber with regions of etched cladding thereby coupling optical energy from the actuation optical fiber to the SMA material in the deflection extent.

5. The shape sensing biopsy needle of claim 1 where the actuation optical fiber is a single-mode fiber with a tilted fiber Bragg grating (TFBG) coupling optical energy from the actuation optical fiber to the SMA material in the deflection extent.

6. The shape sensing biopsy needle of claim 1 where the inner stylet is fabricated from a material which is transparent to infrared optical energy.

7. The shape sensing biopsy needle of claim 1 where the inner stylet is fabricated from polytetrafluoroethylene.

8. The shape sensing biopsy needle of claim 1 where the inner stylet has a longitudinal slot accommodating the SMA material, and a plurality of lumens, one for each actuation optical fiber, and one for the deflection measurement optical fiber.

9. The shape sensing biopsy needle of claim 1 where the SMA is Flexinol wire.

10. A shape sensing biopsy needle comprising an outer stylet and an inner stylet surrounding a central axis,
    the outer stylet comprising a hollow cylinder, the hollow cylinder further comprising, in sequence: a base portion, a needle extent, a first Shape Memory Alloy (SMA) anchor extent, a steering extent, a second SMA anchor extent;
    the steering extent comprising a plurality of parallel slots in the outer stylet, each of the plurality of parallel slots perpendicular to the central axis and terminating in a circular aperture;
    the outer stylet also having an SMA material attached in the first SMA anchor extent and also the second SMA anchor extent and spanning the steering extent;
    the inner stylet comprising:
      a slot for providing clearance to the SMA material;
      at least one actuation optical fiber coupling optical energy to the SMA material in the inner stylet slot and causing a deflection in the steering extent of the outer stylet;
      at least one deflection measurement optical fiber for measuring a deflection, the deflection measurement optical fiber having a plurality of slots formed in the fiber cladding, the slots placed in a plane substantially perpendicular to the fiber axis, the deflection measurement optical fiber having a reflective termination;
      at least one temperature measurement optical fiber sensor.

11. The shape sensing biopsy needle of claim 10 where the slots in the fiber cladding cause a reduction in reflectivity of the optical fiber with increased deflection of the steering extent.

12. The shape sensing biopsy needle of claim 10 where the temperature measurement optical sensor comprises a grating in the at least one activation optical fiber.

13. The shape sensing biopsy needle of claim 10 where the actuation optical fiber is a multi-mode fiber with a side polished region coupled to the SMA material in the deflection extent.

14. The shape sensing biopsy needle of claim 10 where the actuation optical fiber is a multi-mode fiber with regions of etched cladding thereby coupling optical energy from the actuation optical fiber to the SMA material in the deflection extent.

15. The shape sensing biopsy needle of claim 10 where the actuation optical fiber is a single-mode fiber with a tilted fiber Bragg grating (TFBG) coupling optical energy from the actuation optical fiber to the SMA material in the deflection extent.

16. The shape sensing biopsy needle of claim 10 where the inner stylet is fabricated from a material which is transparent to infrared optical energy.

17. The shape sensing biopsy needle of claim 10 where the inner stylet is fabricated from polytetrafluoroethylene.

18. The shape sensing biopsy needle of claim 10 where the inner stylet has a longitudinal slot accommodating the SMA material, and a plurality of lumens, one for each the actuation fiber, and one for the deflection measurement optical fiber.

19. The shape sensing biopsy needle of claim 1 where the SMA is Flexinol wire.

20. A shape sensing biopsy needle comprising:
    an outer stylet and an inner stylet surrounding a central axis,
    the outer stylet comprising a hollow cylinder, the hollow cylinder further comprising, in sequence: a base portion, a needle extent, a first Shape Memory Alloy (SMA) anchor extent, a steering extent, a second SMA anchor extent;

the steering extent comprising a plurality of parallel slots in the outer stylet, each of the plurality of parallel slots perpendicular to the central axis and terminating in a circular aperture;

the outer stylet also having an SMA material attached in the first SMA anchor extent and also the second SMA anchor extent and spanning the steering extent, the SMA activated by optical energy and causing a deflection of the outer stylet steering extent;

the inner stylet comprising:
- a slot for providing clearance to the SMA material;
- at least one deflection measurement optical fiber for measuring a deflection, the deflection measurement optical fiber having a plurality of slots formed in the fiber cladding, the slots placed in a plane substantially perpendicular to the fiber axis, the deflection measurement optical fiber having a reflective termination.

21. The shape sensing needle of claim 20 where the deflection is measured by applying optical energy to the deflection measurement optical fiber and measuring the optical energy reflected from the reflective termination which is not lost by the slots in the fiber cladding.

* * * * *